(12) United States Patent
Valluzzi et al.

(10) Patent No.: US 7,510,540 B2
(45) Date of Patent: Mar. 31, 2009

(54) AUTOTRANSFUSION DEVICE

(75) Inventors: Margherita Valluzzi, San Pietro in Casale (IT); Giampaolo Simonini, Reggio Emilia (IT)

(73) Assignee: Sorin Group Italia S.r.l., Mirandola (MO) (IT)

( * ) Notice: Subject to any disclaimer, the term of this patent is extended or adjusted under 35 U.S.C. 154(b) by 441 days.

(21) Appl. No.: 10/990,341

(22) Filed: Nov. 16, 2004

(65) Prior Publication Data

US 2005/0165343 A1 Jul. 28, 2005

(30) Foreign Application Priority Data

Nov. 28, 2003 (IT) .......................... MI2003A2341

(51) Int. Cl.
- A61M 37/00 (2006.01)
- A61M 1/00 (2006.01)
- B01D 61/00 (2006.01)
- B01D 33/15 (2006.01)
- B04B 3/00 (2006.01)
- B04B 9/10 (2006.01)
- C02F 1/38 (2006.01)

(52) U.S. Cl. .................. 604/5.01; 604/4.01; 604/19; 604/6.1; 604/6.16; 210/645; 210/781; 210/782; 422/44

(58) Field of Classification Search ............... 604/4.01, 604/5.01, 19, 6.01–6.07, 6.1, 6.11, 6.16; 210/645, 781, 782; 422/44
See application file for complete search history.

(56) References Cited

U.S. PATENT DOCUMENTS

| | | | |
|---|---|---|---|
| 3,986,508 A * | 10/1976 | Barrington | 604/411 |
| 4,069,968 A | 1/1978 | Herman | |
| 4,187,979 A * | 2/1980 | Cullis et al. | 494/1 |
| 4,416,654 A * | 11/1983 | Schoendorfer et al. | 494/10 |
| 4,464,167 A * | 8/1984 | Schoendorfer et al. | 604/6.07 |
| 4,668,214 A * | 5/1987 | Reeder | 494/37 |
| 4,935,002 A * | 6/1990 | Gordon | 604/6.09 |
| 5,273,517 A * | 12/1993 | Barone et al. | 494/37 |
| 5,298,016 A * | 3/1994 | Gordon | 604/5.01 |
| 5,702,358 A * | 12/1997 | Witherspoon et al. | 604/6.1 |
| 5,891,080 A * | 4/1999 | Skinkle et al. | 604/6.11 |
| 5,971,948 A * | 10/1999 | Pages et al. | 604/6.02 |

(Continued)

FOREIGN PATENT DOCUMENTS

EP 0 682 953 A1 11/1995

(Continued)

*Primary Examiner*—Leslie Deak
*Assistant Examiner*—Adam Marcetich
(74) *Attorney, Agent, or Firm*—Popovich, Wiles & O'Connell, P.A.

(57) ABSTRACT

An autotransfusion device having: a first line and a first pump, the first line being connected to the inlet of a blood centrifugation cell, and branches of the first line being (i) connected to a red blood cell container, (ii) provided with a coupling, and (iii) being suitable to be connected to the patient; a second line connected to the outlet of a blood centrifugation cell and two branches of the second line being provided with two couplings; and a third line and a second pump, the third line being connected to the first line in an intermediate position between the first pump and the blood centrifugation cell, and branches of the third line (i) being connected to a physiological solution container and (ii) being provided with a coupling.

18 Claims, 4 Drawing Sheets

U.S. PATENT DOCUMENTS

| | | | |
|---|---|---|---|
| 6,284,142 B1 * | 9/2001 | Muller ........................ | 210/745 |
| 6,299,784 B1 | 10/2001 | Biesel | |
| 6,348,156 B1 * | 2/2002 | Vishnoi et al. .............. | 210/739 |
| 6,632,190 B2 | 10/2003 | Simonini et al. | |
| 6,884,228 B2 * | 4/2005 | Brown et al. ................ | 604/6.01 |
| 2001/0044601 A1 * | 11/2001 | Simonini et al. ............ | 604/151 |
| 2002/0099319 A1 * | 7/2002 | Saito et al. .................. | 604/6.04 |
| 2005/0054508 A1 * | 3/2005 | Panzani et al. ................ | 494/37 |

FOREIGN PATENT DOCUMENTS

| | | |
|---|---|---|
| EP | 1 295 619 A2 | 3/2003 |
| WO | WO 03/033066 A2 | 4/2003 |

\* cited by examiner

AUTOTRANSFUSION DEVICE

FIELD OF THE INVENTION

The present invention relates to an autotransfusion device.

BACKGROUND OF THE INVENTION

Surgical operations, particularly those that entail considerable effusion of blood from a patient, are known to require procedures for treating the blood.

A first procedure is preoperative collection. A certain quantity of blood is drawn from the patient and separated into its components, i.e., plasma, platelets, and red blood cells. One or more components are collected to be returned subsequently to the patient during the surgical operation or in the postoperative course, or to obtain derivative products. Other components can be reinfused to the patient immediately.

A second procedure is intraoperative recovery. The blood from the operating field is recovered, with separation and washing of the red blood cells to remove foreign components such as disinfectant and various residues. The red blood cells can be collected for subsequent return to the patient or for immediate reinfusion.

A third procedure is postoperative recovery. The blood from the surgical wound of the patient is recovered, and red blood cells are separated and washed for subsequent return to the patient.

Currently, different machines perform the procedures described above, often entailing operational difficulties and the high costs of single-use circuits and other components. One aim of the present invention is to provide an autotransfusion device that allows the performance of the three procedures alternatively or sequentially on a patient by using a single device and a single use circuit that is mostly unchanged during the three procedures, with the simple addition or replacement of low-cost components for each separate procedure.

SUMMARY OF THE INVENTION

The invention provides an autotransfusion device comprising:

a first line having first and second ends, a first pump providing pumping action for the first line, the first end of the first line being connected to the inlet of a blood centrifugation cell, the second end of the first line being split into first, second, and third branches, the first branch of the first line being connected to a red blood cell container, the second branch of the first line being suitable to be connected to the patient, and the third branch of the first line being provided with a coupling that is suitable to connect the third branch of the first line to a tank for receiving blood recovered from the operating field during an intraoperative recovery procedure;

a second line having first and second ends, the first end of the second line being connected to the outlet of a blood centrifugation cell, the second end of the second line split into first and second branches, the first branch of the second line being provided with a coupling that is suitable to connect the first branch of the second line to a bag for containing at least one of plasma and platelets during a preoperative collection procedure, or to an evacuation bag for intraoperative and postoperative recovery procedures, the second branch of the second line being provided with a coupling that is suitable to connect the second branch of the second line to a bag for containing at least one of plasma and platelets during a preoperative collection procedure; and a third line having first and second ends, a second pump providing pumping action for the third line, the first end of the third line being connected to the first line in an intermediate position between the first pump and the blood centrifugation cell, the second end of the third line being split into first and second branches, the first branch of the third line being connected to a physiological solution container, the second branch of the third line being provided with a coupling that is suitable to connect the second branch of the third line to a bag for containing at least one of plasma and platelets during a preoperative collection procedure and to a bag containing blood recovered from a surgical wound in the postoperative recovery procedure.

The invention also provides methods of using the autotransfusion devices in preoperative, intraoperative, and postoperative recovery procedures.

Additional features and advantages of the invention are set forth in the description which follows and in part will be apparent from the description. The objectives and other advantages of the invention will be realized and attained by the device as particularly pointed out in the written description and claims.

It is to be understood that both the foregoing general description and the following detailed description are exemplary and explanatory and are intended to provide further explanation of the invention as claimed.

BRIEF DESCRIPTION OF THE DRAWINGS

Further characteristics and advantages will become better apparent from the description of a preferred but not exclusive embodiment of the invention, illustrated by way of non-limiting example in the accompanying drawings.

DETAILED DESCRIPTION OF EMBODIMENTS OF THE INVENTION

Figure 1:
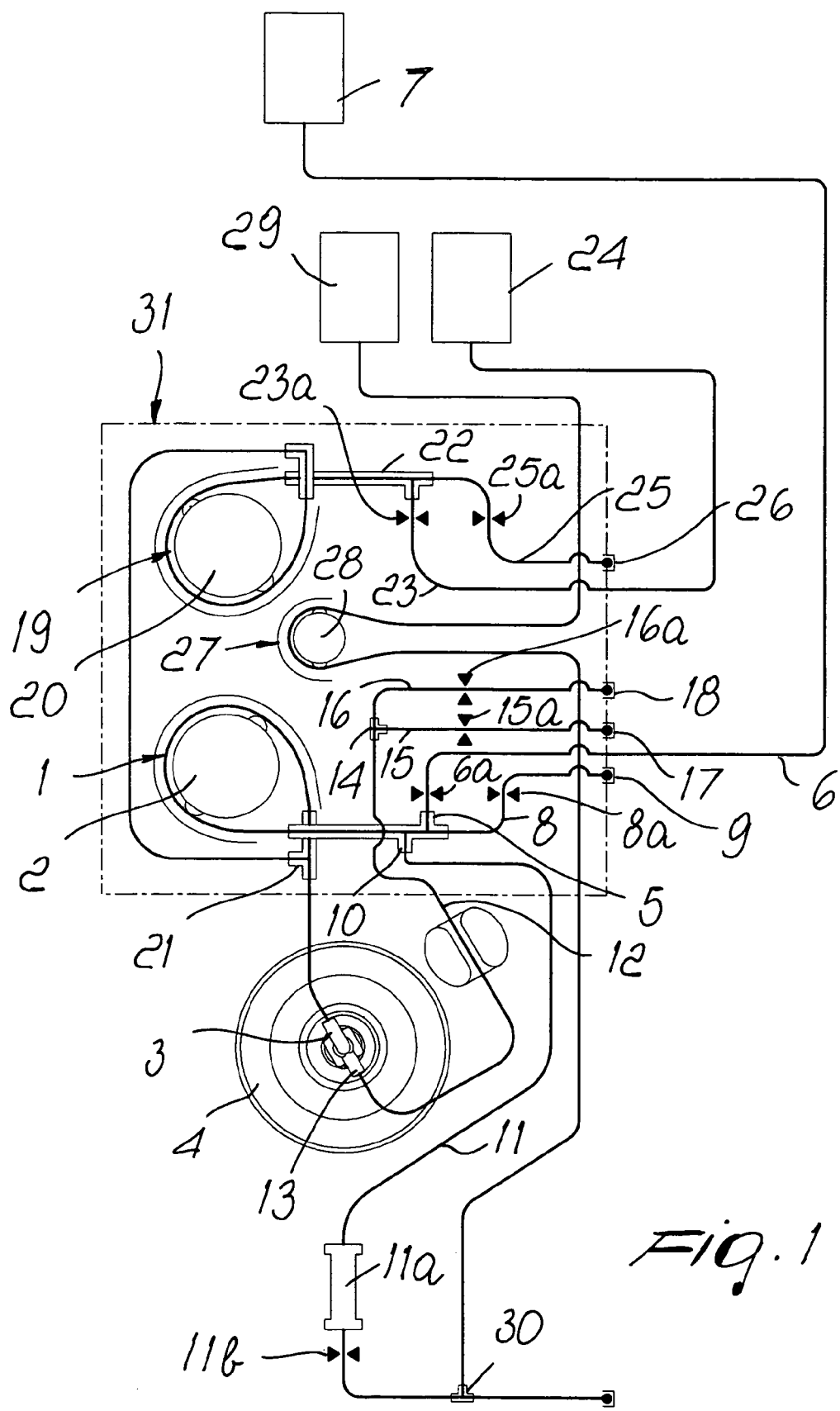
FIG. 1 is a view of all the components of an autotransfusion device that remain unchanged during the three possible procedures.

An autotransfusion device of the invention can be used, alternatively or sequentially, for preoperative collection procedures, intraoperative, and postoperative recovery procedures.

The invention provides an autotransfusion device comprising:

a first line having first and second ends, a first pump providing pumping action for the first line, the first end of the first line being connected to the inlet of a blood centrifugation cell, the second end of the first line being split into first, second, and third branches, the first branch of the first line being connected to a red blood cell container, the second branch of the first line being suitable to be connected to the patient, and the third branch of the first line being provided with a coupling that is suitable to connect the third branch of the first line to a tank for receiving blood recovered from the operating field during an intraoperative recovery procedure;

a second line having first and second ends, the first end of the second line being connected to the outlet of a blood centrifugation cell, the second end of the second line split into first and second branches, the first branch of the second line being provided with a coupling that is suitable to connect the first branch of the second line to a bag for containing at least one of plasma and platelets during a preoperative collection procedure, or to an evacuation bag for intraoperative and postoperative recovery procedures, the second branch of the second line being provided with a coupling that is suitable to connect the second branch of the second line to a bag for containing at least one of plasma and platelets during a preoperative collection procedure; and a third line having first and second ends, a second pump providing pumping action for the third line, the first end of the third line being connected to the first line in an intermediate position between the first pump and the blood centrifugation cell, the second end of the third line being split into first and second branches, the first branch of the third line being connected to a physiological solution container, the second branch of the third line being provided with a coupling that is suitable to connect the second branch of the third line to a bag for containing at least one of plasma and platelets during a preoperative collection procedure and to a bag containing blood recovered from a surgical wound in the postoperative recovery procedure.

In an embodiment of the invention, the autotransfusion device further comprises a fourth line having first and second ends and a third pump providing pumping action for the fourth line, the first end of the fourth line being connected to an anticoagulant container, the second end of the fourth line being connected to the second branch of the first line that is suitable to be connected to the patient.

In an embodiment of the invention, one or more of the lines are disposed in a supporting box. In an embodiment of the invention, one or more of the lines are single-use lines. In another embodiment of the invention, one or more of the pumps are peristaltic pumps. In an embodiment of the invention, each pump is a peristaltic pump.

The invention provides a method of performing a preoperative collection procedure with an autotransfusion device described herein comprising: pumping blood from a patient to the centrifugation cell to separate the blood into its components. In an embodiment of the invention, the plasma and platelet components of the blood are collected either separately or together. In another embodiment, the plasma and platelet components of the blood are collected separately. In an embodiment of the invention, red blood cells are collected and reinfused into the patient.

The invention provides a method of performing an intraoperative recovery procedure with an autotransfusion device described herein comprising: conducting blood recovered from the operating field to the centrifugation cell; and separating supernatant from red blood cells in the centrifugation cell. In an embodiment of the invention, the method further comprises washing the red blood cells in the centrifugation cell. In an embodiment of the invention, washing the red blood cells includes adding physiological solution to the red blood cells in the centrifugation cell. In an embodiment of the invention, the method further comprises reinfusing red blood cells into the patient.

The invention provides a method of performing a postoperative recovery procedure with an autotransfusion device described herein comprising: collecting blood recovered from a surgical wound of the patient; transferring the blood to the centrifugation cell; and separating supernatant from red blood cells in the centrifugation cell. In an embodiment of the invention, the method further comprises washing the red blood cells in the centrifugation cell. In an embodiment of the invention, washing the red blood cells includes adding physiological solution to the red blood cells in the centrifugation cell. In an embodiment of the invention, the method further comprises reinfusing red blood cells into the patient.

In one embodiment, the invention provides an autotransfusion device comprising:

a first single-use line, which is managed by a first pump that is connected at one end to the intake connector of a blood centrifugation cell and splits at the other end by virtue of the presence of a first three-way connector into a first branch, which is connected to a bag meant to contain red cells, and a second branch, provided with a coupling that is suitable to be connected, in the intraoperative recovery procedure, to a tank that receives the blood lost in the operating field, a second three-way connector for the branching of a line for connection to the patient being provided in the portion comprised between the pump and the first three-way connector;

a second single-use line, which is connected to the output connector of the centrifugation cell and splits into a first branch, which is provided with a coupling that is suitable to be connected selectively to a bag meant to contain one of the blood components constituted by plasma and platelets that is meant to be collected during the preoperative collection procedure and to an evacuation bag in the intraoperative and postoperative recovery procedures, and into a second branch, which is provided with a coupling that is suitable to be connected, in the preoperative collection procedure, to a bag meant to contain at least one of the components constituted by plasma and platelets meant to be collected or reinfused;

a third single-use line, which is managed by a second pump, which is connected at one end to a three-way connector arranged on the line managed by the first pump in an intermediate position between said pump and the blood centrifugation cell and splits at the other end into a first branch, which is connected to a bag meant to contain physiological solution, and a second branch, which is provided with a coupling that is suitable to be connected selectively to the bag meant to contain at least one of the components constituted by plasma and platelets meant to be collected or reinfused in the preoperative collection procedure and to a bag for containing the blood spilled by the wound in the postoperative recovery procedure;

a fourth single-use line, managed by a third pump for transferring anticoagulant from a containment bag to the line for connection to the patient; and clamps for blocking the single-use lines.

FIG. 1 shows an autotransfusion device with all of the components that remain unchanged during the preoperative collection procedure, the intraoperative recovery procedure, and the postoperative recovery procedure. With reference to FIG. 1, a first peristaltic pump 2 provides pumping action for a first single-use line 1. The first line 1 has first and second ends. The first end connects to the intake connector 3 of the centrifugation cell 4, suitable to separate blood into three components, i.e., plasma, platelets, and red blood cells.

At the second end of the first line 1, the three-way connector 5 splits the first line 1 into a first branch 6 and a second branch 8. The first branch 6 connects to a bag 7, which is meant to contain the red blood cells. The second branch 8 has a coupling 9. A three-way connector 10 is located in the portion of first line 1 between the pump 2 and the connector 5 for branching of line 11, which has a drip feed 11a, and which connects to the patient.

The second single-use line 12 connects to the output connector 13 of the centrifugation cell 4. A three-way connector 14 splits the second line 12 into first and second branches 15 and 16, respectively, which have the couplings 17 and 18.

The second peristaltic pump 20 manages a third single-use line 19. The third line 19 has first and second ends. The first end of the third line 19 connects to the three-way connector 21 on the first line 1 in output from the first pump 2. The three-way connector 22 splits the second end of the third line 19 into a first branch 23 and a second branch 25. The first branch 23 connects to the bag 24, which is meant to contain physiological solution. The second branch 25 has a coupling 26.

The peristaltic pump 28 provides pumping action to the fourth single-use line 27 to transfer anticoagulant from the bag 29 to the three-way connector 30 inserted on the line 11 when blood is drawn from the patient. The embodiment of the autotransfusion device illustrated in FIG. 1 has clamps for clamping the single-use lines to allow performing the various intended procedures. The clamps 6a, 8a, 11b, 15a, 16a, 23a, and 25a are provided on the lines 6, 8, 11, 15, 16, 23, and 25, respectively. A tubing organizer 31 supports the single-use lines. All the components described in FIG. 1 remain unchanged during the three procedures, which can be performed as described below.

Figure 2:
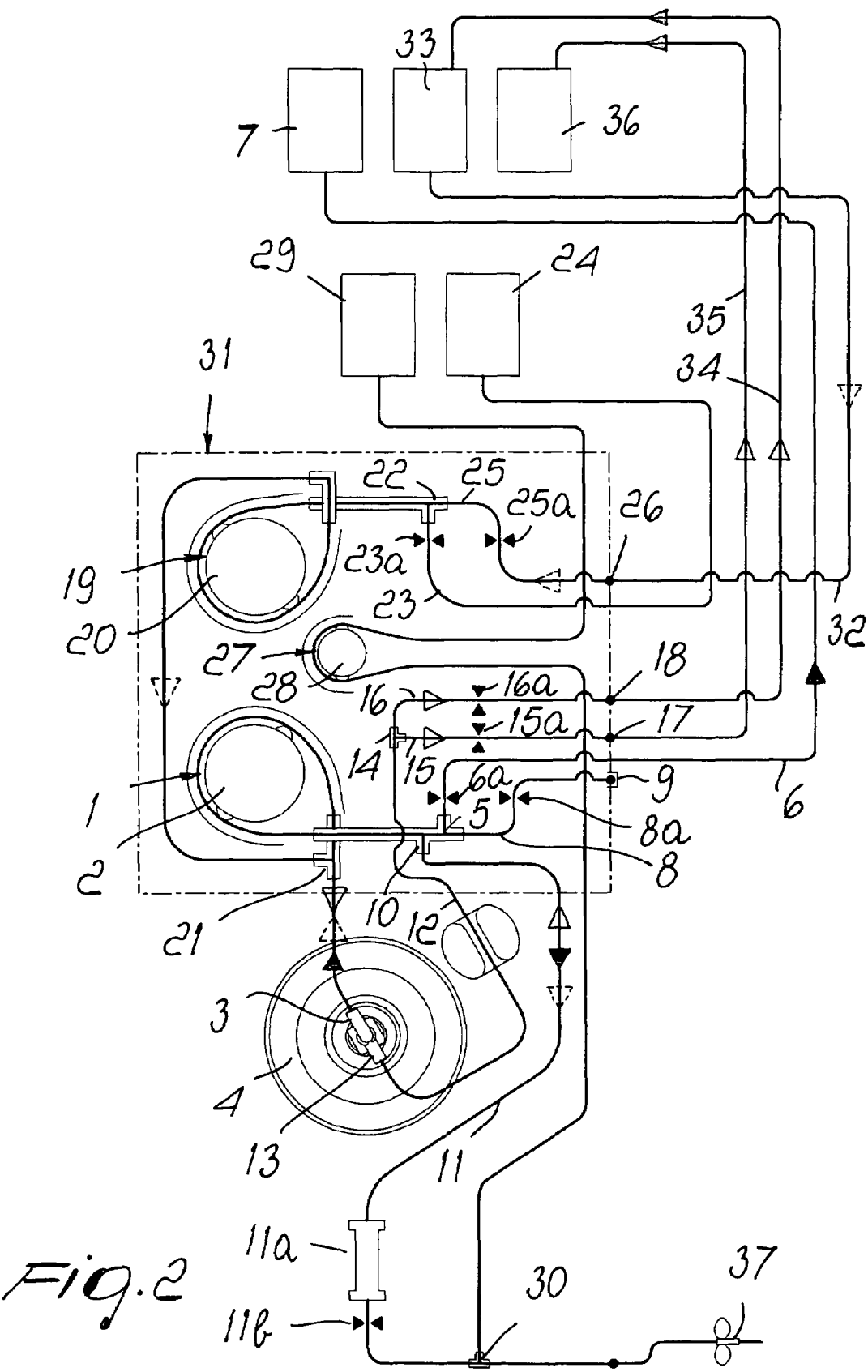
FIG. 2 is a view of the configuration of the autotransfusion device to perform a preoperative collection procedure.

FIG. 2 illustrates the configuration of the autotransfusion device for the preoperative collection procedure. To perform this procedure, the coupling 26 is connected to a first bag 33 by the line 32, the coupling 18 is connected to the first bag 33 by the line 34, and the coupling 17 is connected to the second bag 36 by the line 35. A needle 37 is inserted into the end of the line 11.

The first step of the preoperative collection procedure, shown in FIG. 2 by arrows drawn in solid lines, is drawing blood from the patient. The first pump 2 rotates clockwise and sends blood, coming from the line 11, into the centrifugation cell 4, which is rotating to separate the blood into its components. First plasma and then platelets are output from the centrifugation cell 4 through the second line 12. If at least one of these blood components (plasma or platelets) is to be collected, one blood component is sent to the first bag 33 and the other blood component is sent to the second bag 36. The blood component sent to the first bag 33 can be collected or reinfused to the patient. If instead both of these blood components (plasma and platelets) are to be reinfused to the patient and only red blood cells are to be collected, the blood components (plasma and platelets) can both be sent to the first bag 33.

The plasma and platelets can be separated by methods known to one of skill in the art. See, for example, U.S. Pat. Nos. 6,284,142 B1 and 6,348,156 B1, and U.S. patent application Ser. No. 10/898,720, filed Jul. 23, 2004, entitled "Control Device for the Separate Collection of Blood Components in Output From a Blood Centrifugation Cell", the contents of each of which are hereby incorporated by reference herein.

The second step of the procedure, shown in FIG. 2 by black arrows, is treating the red blood cells. The red blood cells remain in the centrifugation cell 4 at the end of the first step. By reversing the direction of rotation of the first pump 2, the red blood cells are extracted from the centrifugation cell 4. Line 6 conducts the red blood cells to the bag 7, if red blood cells are to be collected, or they can be reinfused to the patient by the line 11.

The third step of the procedure, shown in FIG. 2 by arrows drawn in dashed lines, is reinfusing the contents of the first bag 33 to the patient. The second pump 20 rotates counterclockwise and conveys the contents of the bag 33 to the coupling 21. If the centrifugation cell 4 contains red blood cells to be reinfused into the patient, the first pump 2 operates in series with the second pump 20 but at a higher flow rate than the second pump 20, and line 11 is directed to the patient. If instead the centrifugation cell 4 is empty because the red blood cells are contained in the bag 7, the first pump 2 operates in series with the second pump 20 and at the same flow-rate, and therefore only the contents of the first bag 33 reach the line 11.

Figure 3:
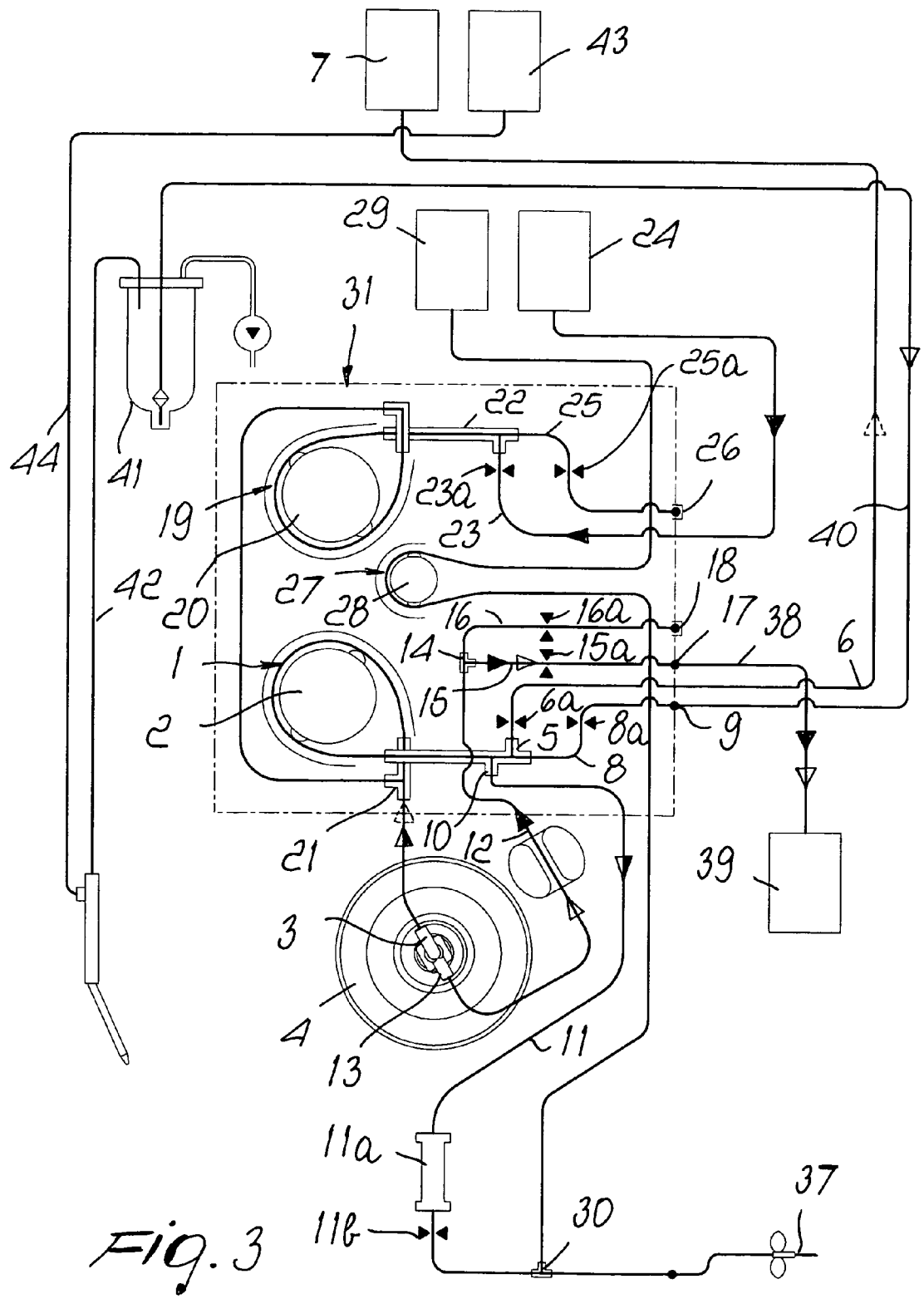
FIG. 3 is a view of the configuration of the autotransfusion device to perform an intraoperative recovery procedure.

FIG. 3 illustrates the configuration of the autotransfusion device for the intraoperative recovery procedure. To perform the intraoperative recovery procedure, the coupling 17 is connected to the evacuation bag 39 by the line 38 and the coupling 9 is connected to the reservoir 41 by the line 40. In a known manner, the reservoir 41 receives the blood recovered from the operating field, aspirated by the line 42 with the addition of anticoagulant conveyed from the bag 43 by the line 44. The needle 37 is again present at the end of the line 11.

The first step of the intraoperative recovery procedure, shown in FIG. 3 by arrows drawn in solid lines, is to fill the centrifugation cell 4 from the tank 41 with blood recovered from the operating field. The first pump 2 rotates clockwise and the blood enters the rotating centrifugation cell 4. The lines 12, 15, 38 conduct supernatant to the evacuation bag 39, while the red blood cells remain in the centrifugation cell 4.

The second step, shown in FIG. 3 by black arrows, is washing the red blood cells contained in the centrifugation cell 4. After stopping the first pump 2, the second pump 20 starts and draws physiological solution from the bag 24 through the line 23 and sends it to the centrifugation cell 4, with subsequent outflow toward the evacuation bag 39.

There are two options for the third step of treating the red blood cells contained in the centrifugation cell. According to the first option, shown in FIG. 3 by arrows drawn in broken lines, the red blood cells are aspirated by the first pump 2 and sent by the line 6 to the bag 7. According to the second option, shown in FIG. 3 by black-and-white arrows, the red blood cells are reinfused to the patient through the line 11.

Figure 4:
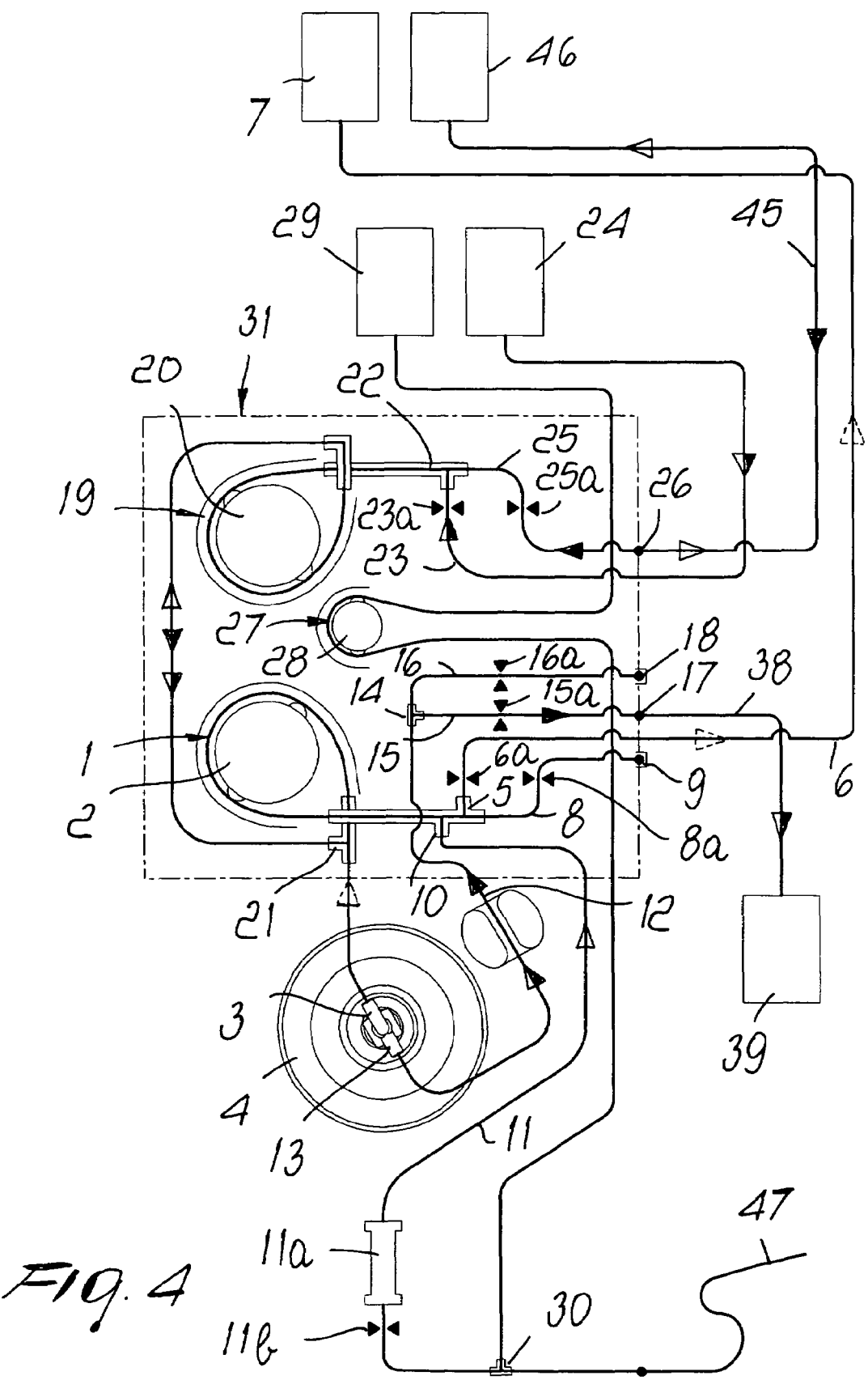
FIG. 4 is a view of the configuration of the autotransfusion device to perform a postoperative recovery procedure.

FIG. 4 illustrates the configuration of the autotransfusion device for the postoperative recovery procedure. To perform the postoperative recovery procedure, the coupling 26 is connected, by the line 45, to the bag 46 for containing the blood recovered from the surgical wound of the patient. The coupling 17 remains connected by the line 38 to the evacuation bag 39. The drainage tube 47 is provided at the end of the line 11.

The first step of the postoperative recovery procedure, shown in FIG. 4 by arrows drawn in solid lines, is filling the bag 46. The first pump 2, rotating clockwise, aspirates blood from the drainage tube 47 and sends it to the second pump 20, also rotating clockwise and with the same flow-rate. The first pump 2 fills the bag 46 through the lines 25 and 45.

The second step, shown in FIG. 4 by black arrows, is transferring the blood contained in the bag 46 to the rotating centrifugation cell 4 by the second pump 20, which has reversed its direction of rotation to counterclockwise. The red blood cells remain in the centrifugation cell 4 and the supernatant flows into the evacuation bag 39.

In the third step, shown in FIG. 4 by black-and-white arrows, the red blood cells contained in the centrifugation cell 4 are washed. The second pump 20 continues to rotate counterclockwise and sends physiological solution from the bag 24 to the centrifugation cell 4, with exit of the liquid toward the evacuation bag 39.

The fourth step of the postoperative recovery procedure, shown in FIG. 4 by arrows drawn in broken lines, is sending the red blood cells contained in the centrifugation cell 4 to the bag 7, which is performed by the first pump 2 rotating counterclockwise.

The above description and accompanying drawings are provided for the purpose of describing embodiments of the invention and are not intended to limit the scope of the invention in any way. It will be apparent to those skilled in the art that various modifications and variations can be made in the devices and methods without departing from the spirit or scope of the invention. For example, the line supporting tubing organizer 31 might be omitted. Thus, it is intended that the present invention cover the modifications and variations of this invention provided they come within the scope of the appended claims and their equivalents.

What is claimed is:

1. An autotransfusion device comprising:
a first line having first and second ends, a first pump providing pumping action for the first line, the first pump being disposed between the first and second ends of the first line, the first end of the first line being connected to the inlet of a blood centrifugation cell, the second end of the first line being split into first, second, and third branches, the first branch of the first line being connected to a red blood cell container, the second branch of the first line being suitable to be connected to the patient, and the third branch of the first line being provided with a coupling that is suitable to connect the third branch of the first line to a reservoir for receiving blood recovered from the operating field during an intraoperative recovery procedure;
a second line having first and second ends, the first end of the second line being connected to the outlet of a blood centrifugation cell, the second end of the second line split into first and second branches, the first branch of the second line being provided with a coupling that is suitable to connect the first branch of the second line to a bag for containing at least one of plasma and platelets during a preoperative collection procedure, or to an evacuation bag for intraoperative and postoperative recovery procedures, the second branch of the second line being provided with a coupling that is suitable to connect the second branch of the second line to a bag for containing at least one of plasma and platelets during a preoperative collection procedure; and
a third line having first and second ends, a second pump providing pumping action for the third line, the second pump being disposed between the first and second ends of the third line, the first end of the third line being connected to the first line in an intermediate position between the first pump and the blood centrifugation cell, the second end of the third line being split into first and second branches, the first branch of the third line being connected to a physiological washing solution container, the second branch of the third line being provided with a coupling that is suitable to connect the second branch of the third line to a bag for containing at least one of plasma and platelets dining a preoperative collection procedure, or to a bag containing blood recovered from a surgical wound in a postoperative recovery procedure.

2. The autotransfusion device according to claim 1, further comprising a fourth line having first and second ends, a third pump providing pumping action for the fourth line, the first end of the fourth line being connected to an anticoagulant container, the second end of the fourth line being connected to the second branch of the first line that is suitable to be connected to the patient.

3. The autotransfusion device according to claim 1, wherein one or more of the lines are disposed in a tubing organizer.

4. The autotransfusion device according to claim 1, wherein one or more of the lines are single-use lines.

5. The autotransfusion device according to claim 1, wherein one or more of the pumps are peristaltic pumps.

6. The autotransfusion device according to claim 1, wherein each pump is a peristaltic pump.

7. A method of performing a preoperative collection procedure with an autotransfusion device of claim 1, comprising:
pumping blood from a patient to the centrifugation cell to separate the blood into its components.

8. A method according to claim 7, wherein plasma and platelet components of the blood are collected either separately or together.

9. A method according to claim 8, wherein the plasma and platelet components of the blood are collected separately.

10. A method according to claim 7, wherein red blood cells are collected and reinfused into the patient.

11. A method of performing an intraoperative recovery procedure with an autotransfusion device of claim 1, comprising:
conducting blood recovered from the operating field to the centrifugation cell; and
separating supernatant from red blood cells in the centrifugation cell.

12. A method according to claim 11, further comprising washing the red blood cells in the centrifugation cell.

13. A method according to claim 12, wherein washing the red blood cells includes adding physiological washing solution to the red blood cells in the centrifugation cell.

14. A method according to claim 11, further comprising reinfusing red blood cells into the patient.

15. A method of performing a postoperative recovery procedure with an autotransfusion device of claim 1, comprising:
collecting blood recovered from a surgical wound of the patient;
transferring the blood to the centrifugation cell; and
separating supernatant from red blood cells in the centrifugation cell.

16. A method according to claim 15, further comprising washing the red blood cells in the centrifugation cell.

17. A method according to claim 16, wherein washing the red blood cells includes adding physiological washing solution to the red blood cells in the centrifugation cell.

18. A method according to claim 15, further comprising reinfusing red blood cells into the patient.

* * * * *